United States Patent
Linders et al.

(10) Patent No.: US 6,215,848 B1
(45) Date of Patent: Apr. 10, 2001

(54) FORMING AN ASSEMBLED IMAGE FROM SUCCESSIVE X-RAY IMAGES

(75) Inventors: Petrus W. J. Linders; Alexander H. W. Van Eeuwijk, both of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/208,508

(22) Filed: Dec. 9, 1998

(30) Foreign Application Priority Data

Dec. 10, 1997 (EP) .................................................. 97203874

(51) Int. Cl.[7] .............................. A61B 6/03; H05G 1/64
(52) U.S. Cl. ................ 378/98.12; 378/98.8; 250/370.09; 382/294
(58) Field of Search .................... 378/98.8, 98.12, 378/98.11, 62; 250/370.09; 382/132, 294

(56) References Cited

U.S. PATENT DOCUMENTS

| 4,636,953 | 1/1987 | Kageyama | 378/98.12 |
| 5,373,543 | * 12/1994 | Ackermann et al. | 378/98.12 |
| 5,463,668 | * 10/1995 | Kagaya | 378/98.12 |
| 5,544,215 | * 8/1996 | Shroy, Jr. et al. | 378/98.12 |
| 5,644,613 | * 7/1997 | Mick | 378/98.12 |
| 5,864,146 | * 1/1999 | Karellas | 378/98.8 |
| 5,912,942 | * 6/1999 | Schick et al. | 378/98.12 |
| 6,021,173 | * 2/2000 | Brauers et al. | 378/98.8 |
| 6,041,097 | * 3/2000 | Roos et al. | 378/62 |

FOREIGN PATENT DOCUMENTS 19613662  10/1997  (DE) ................................. A61B/6/00

* cited by examiner

Primary Examiner—Robert H. Kim
Assistant Examiner—Drew A. Dunn
(74) Attorney, Agent, or Firm—John F. Vodopia

(57) ABSTRACT

A method for forming an assembled image from successive sub-images comprises the step of acquiring the sub-images, notably X-ray images, with an X-ray detector comprising an essentially flat X-ray-sensitive surface. An X-ray examination apparatus comprises an X-ray detector having a flat X-ray sensitive surface. Advantageously, difference images are derived from successive sub-images. For example, the assembled image derived from the difference images is used to display blood flow patterns in a patient's vascular system.

14 Claims, 5 Drawing Sheets

FORMING AN ASSEMBLED IMAGE FROM SUCCESSIVE X-RAY IMAGES

BACKGROUND OF THE INVENTION

1. Field of the Invention

The invention relates to a method of deriving an assembled image from successive X-ray images. The invention also relates to an X-ray examination apparatus which is suitable for deriving an assembled image from successive X-ray images.

2. Description of Related Art

A method and an X-ray examination apparatus of this kind are known from European patent application EP 0 655 861.

According to the known method the successive X-ray images are picked up by means of an image intensifier pick-up chain which includes an X-ray image intensifier and a television camera. A series of successive X-ray images of the relevant parts of the patient is formed on an entrance screen of the X-ray image intensifier by irradiating separate parts of an object, for example a patient to be radiologically examined, by means of an X-ray beam; these X-ray images are converted into successive optical images which appear on the exit window of the X-ray image intensifier and electronic video signals are derived from the successive optical images by means of the television camera. An image processing unit forms an image signal representing the assembled image from the electronic video signals. The assembled image reproduces the individual parts of the patient together in a single image.

Because the known method utilizes an X-ray image intensifier, merely a comparatively narrow strip at the center of the successive individual X-ray images can be used. The use of the X-ray image intensifier introduces distortions in the optical image; these distortions are pronounced notably at the edge of the optical image. One cause of the distortions is the cushion distortion in the X-ray image which is due to the curvature of the entrance screen. Despite the fact that only narrow strips at the center of respective X-ray images, where the distortion is lowest, are used, according to the known method extensive operations must be performed so as to produce an assembled image which does not contain an excessive amount of distortion. Because only narrow strips of the successive X-ray images can be used, the known method requires a comparatively large number of X-ray images so as to form an assembled image of an elongate part of the patient. Notably peripheral angiography, being the imaging of blood vessels in an arm or a leg of a patient, requires the formation of a large number of X-ray images which may even reach a few dozen. Consequently, the patient to be examined is exposed to a rather high X-ray dose.

SUMMARY OF THE INVENTION

It is an object of the invention to provide a method for deriving an assembled image from successive X-ray images which requires substantially fewer X-ray images, in comparison with the known method, so as to produce an assembled image of high diagnostic quality. It is a further object of the invention to provide a method which, in comparison with the known method, requires substantially fewer operations so as to produce an assembled image of high diagnostic quality.

This object is achieved by means of a method according to the invention which is characterised in that the X-ray images are picked up by means of an X-ray detector having a predominantly flat X-ray sensitive surface.

The X-ray-sensitive surface of the X-ray detector is flat to such a degree that the X-ray images are formed on the X-ray-sensitive surface substantially without geometric image distortions. Any image distortion occurring nevertheless will be so small that it does not affect the diagnostic quality of the individual X-ray images. This means that hardly any or even no corrections will be required for suitably visible reproduction of small details upon display of the image information of the X-ray images, and that the anatomic details in the image will not be distorted or only hardly so. Therefore, the image information contained in the X-ray images is suitable for diagnostic purposes.

Using the method according to the invention, even in the case of an elongate scene such as the limbs of a patient very few successive X-ray images will be required so as to form an assembled image which reproduces substantially the entire scene without essential distortions. Because only a few X-ray images are required according to the invention, the patient to be examined is exposed to an X-ray dose which is much smaller than that required according to the known method.

These and other aspects of the invention will be elaborated on the basis of the embodiments as defined in the dependent Claims.

An image sensor matrix constitutes a suitable X-ray detector for the method according to the invention. Such an image sensor matrix includes, for example X-ray sensitive sensor elements which are arranged in a matrix. Individual sensor elements are coupled to a read-out line by means of a switching element. Individual switching elements are coupled to a control line. Incident X-rays are converted into electric charges in the sensor elements. The sensor elements are made of, for example a material which converts X-rays into electric charges, for example amorphous hydrated silicon ($\alpha$-Si:H) or an X-ray sensitive photoconductor such as selenium (Se) or lead oxide (PbO). Alternatively, the sensor elements can be constructed as infrared sensitive, ultraviolet sensitive or light sensitive elements, such as photodiodes or phototransistors; in that case the image sensor matrix also includes a conversion layer for converting incident X-rays into radiation whereto the sensor elements are sensitive. The conversion layer is, for example a doped cesium iodide (CsI) layer. An image sensor matrix of this kind predominantly has a flat X-ray sensitive surface so that hardly any geometrical distortions occur during the picking up of an X-ray image. The image sensor matrix derives sub-image signals from individual X-ray images. Such a sub-image signal is derived from the electric charges read out from the sensor elements via the read-out lines. In order to read out the sensor elements, the switching elements are controlled by way of signals which are supplied via the control lines. Such sub-image signals are processed in an image processing unit so as to form an image signal for the assembled image.

Another embodiment of the X-ray detector preferably includes a conversion screen provided with an essentially flat layer of scintillation material, for example doped cesium iodide (CsI). The X-ray images are formed substantially without distortion on the conversion screen. The conversion screen converts an X-ray image into a radiation image of infrared or ultraviolet radiation or visible light. Sub-image signals are derived from individual radiation images by means of one or more image sensors. The image processing unit processes such sub-image signals so as to form an image signal for the assembled image.

Furthermore, the image information of the successive X-ray images can be combined so as to form a single assembled image. This assembled image reproduces, by way of a single image, a scene which is so large that the scene cannot be reproduced (or only with great difficulty) in an X-ray image in one step. For example, this scene is extremely elongate, for example the legs of the patient. Reproducing the entire scene in a single image offers the radiologist an effective survey of said scene, for example the vascular system in the legs of the patient. Sub-image signals derived from the individual X-ray images are preferably merged so as to form such an image signal representing the assembled image. Because hardly any distortions occur during the formation of the individual X-ray images, hardly any corrections will be required for the individual sub-image signals. For merging it may be necessary to take into account overlap between successive X-ray images.

Furthermore, it is advantageous to form subtraction images from successive X-ray images. Brightness values of individual difference images represent differences between corresponding brightness values of successive X-ray images. The object to be examined is notably a patient to be radiologically examined, notably a part of the vascular system thereof. The successive X-ray images are formed by irradiating the patient after a contrast medium is injected into the patient's vascular system. The difference images show a double contrast which reproduces the progression of the contrast medium in the blood vessels of the patient. At the area where contrast medium is reproduced in the last X-ray image formed but not yet in the corresponding part of the preceding X-ray image, for example high grey values are formed. At the area where a concentration of contrast medium is reproduced in the preceding X-ray image which is higher than that in the corresponding part of the last X-ray image formed, low grey values are formed. It will be evident to those skilled in the art that high and low grey values can be interchanged, because the negative image actually contains the same image information as the corresponding positive image. The difference images always show two grey value transitions which correspond to the appearance and disappearance, respectively, of the concentration of contrast medium in a blood vessel of the patient in the relevant part of a blood vessel reproduced in the successive X-ray images. The progression of the contrast medium can be accurately followed on the basis of the double contrast in the X-ray images. The assembled image contains the overall image information of the difference images and reproduces an overall survey of the blood flow in the vascular system of a part of the patient, for example in the legs of the patient, in a single image. The assembled image is formed by merging image information of respective difference images.

Because the X-ray detector causes hardly any or no distortions in the X-ray images, the blood flow in the vascular system is also reproduced without distortions in the assembled image, so with a high diagnostic quality. For the formation of the difference images it is not necessary to form a separate mask image. A preceding X-ray image acts as if it were a mask image for an individual X-ray image. The X-ray dose required to image the vascular system with a suitable diagnostic quality is thus substantially reduced in comparison with the conventional method.

The assembled image is derived from the difference images, each of which represents a difference between successive X-ray images at substantially equal intervals. Such an assembled image contains information as regards the flow velocity pattern in the vascular system of the patient. This flow velocity pattern can be accurately derived from the assembled image on the basis of the double contrast in the difference images. This flow velocity pattern can be readily reproduced in the assembled image, for example while using so-called false colors. Such an assembled image, reproducing the flow velocity pattern and involving hardly any distortion, is a particularly suitable technical aid for making a suitable diagnosis in respect of vascular problems.

Time intervals between successive X-ray images are controlled on the basis of the progression of the contrast liquid. For example, said successive time intervals are adjusted in such a manner that the front of the contrast liquid in a vessel of the patient is always reproduced. approximately at the center of the individual X-ray images. The front of the contrast liquid in the vascular system of the patient can be observed by way of X-ray fluoroscopy. The flow velocity pattern in the relevant blood vessel can be picked up by measurement of the time intervals. Because hardly any distortion occurs in the X-ray images, the flow velocity can be derived with high precision. The flow velocity is calculated on the basis of the brightness values of the difference images, notably the movement of the double contrasts in the respective difference images provide an accurate result for the flow velocity of the blood in the patient. Especially the flow velocity in the patient's legs is accurately determined. The flow velocity can either be calculated from the difference images or from the assembled image which also contains brightness values of the difference images. In particular the assembled image contains the flow velocity pattern in substantially the entire vascular system of e.g. the patient's legs. Thus, the assembled image is a useful technical aid for displaying the flow velocity pattern so as to diagnose vascular disorders.

The X-ray beam is preferably limited by arranging X-ray absorption means in the X-ray beam. The X-ray absorption means are, for example collimator elements which stop the X-rays substantially completely or filter elements which partly attenuate the X-rays. Such X-ray absorption means are arranged between the X-ray source and the X-ray detector, preferably between the X-ray source and the patient to be examined. On the basis of the position of the contrast medium the X-ray absorption means are arranged in such a manner that predominantly it is only the part of the vascular system of the patient which has just been reached by the contrast medium that is exposed to the X-rays. The X-ray absorption means are accurately positioned on the basis of the double contrast so as to achieve accurate exposure of the patient. It is thus ensured that the patient does not receive any unnecessary X-rays, the region to be examined nevertheless being completely reproduced in the X-ray images.

Because hardly any or no distortion occurs during the formation of the X-ray images by means of a flat X-ray detector, corrections for motions of the patient can be readily executed. Preferably prior to the formation of the assembled image, variations in the X-ray images due to small motions are practically completely corrected by shifting individual X-ray images relative to one another over a few pixels with respect to the scene.

It is another object of the invention to provide an X-ray examination apparatus which enables, while utilizing a small number of X-ray images, the formation of an assembled image of high diagnostic quality of a scene which is substantially larger than can be reproduced in a single X-ray image.

This object is achieved by means of an X-ray examination apparatus according to the invention which is characterised in that the X-ray detector is provided with a predominantly flat X-ray-sensitive surface.

An X-ray examination apparatus of this kind includes an X-ray detector for deriving image signals from successive X-ray images and an image processing unit for deriving an image signal representing image information of the assembled image from the image signals. Such an X-ray examination apparatus according to the invention is suitable for carrying out the method according to the invention. It is thus achieved that X-ray images are formed substantially without distortion, so that it is only necessary to merge image information from very few X-ray images so as to reproduce the large scene in the single assembled image without serious distortions.

It is another object of the invention to provide an X-ray examination apparatus which enables accurate reproduction of differences between successive X-ray images and in which a substantially lower X-ray dose is required and fewer correction operations are necessary in comparison with the known X-ray examination apparatus.

This object is achieved by means of an X-ray examination apparatus according to the invention which is characterised in that the X-ray examination apparatus is arranged to derive difference images from successive X-ray images and to derive the assembled image from said difference images.

Such an X-ray examination apparatus includes an image processing unit which is provided with a substraction unit for deriving a difference signal from said image signals, said difference signal representing differences between corresponding brightness values of successive X-ray images. An X-ray examination apparatus of this kind is particularly suitable for carrying out the method of the invention disclosed in claim 5. Consequently, an X-ray examination apparatus of this kind is suitable for deriving difference images from only a small number of X-ray images and for merging the image information of the difference images so as to form the assembled image. Because the X-ray images are hardly distorted and only few X-ray images are required, hardly any image corrections be performed. For example, it is only necessary to take into account an overlap between successive X-ray images.

BRIEF DESCRIPTION OF THE DRAWING

These and other aspects of the invention will become apparent from and will be elucidated with reference to the embodiments described hereinafter with reference to the accompanying drawing; therein.

DETAILED DESCRIPTION OF THE PREFERRED EMBODIMENT

Figure 1:
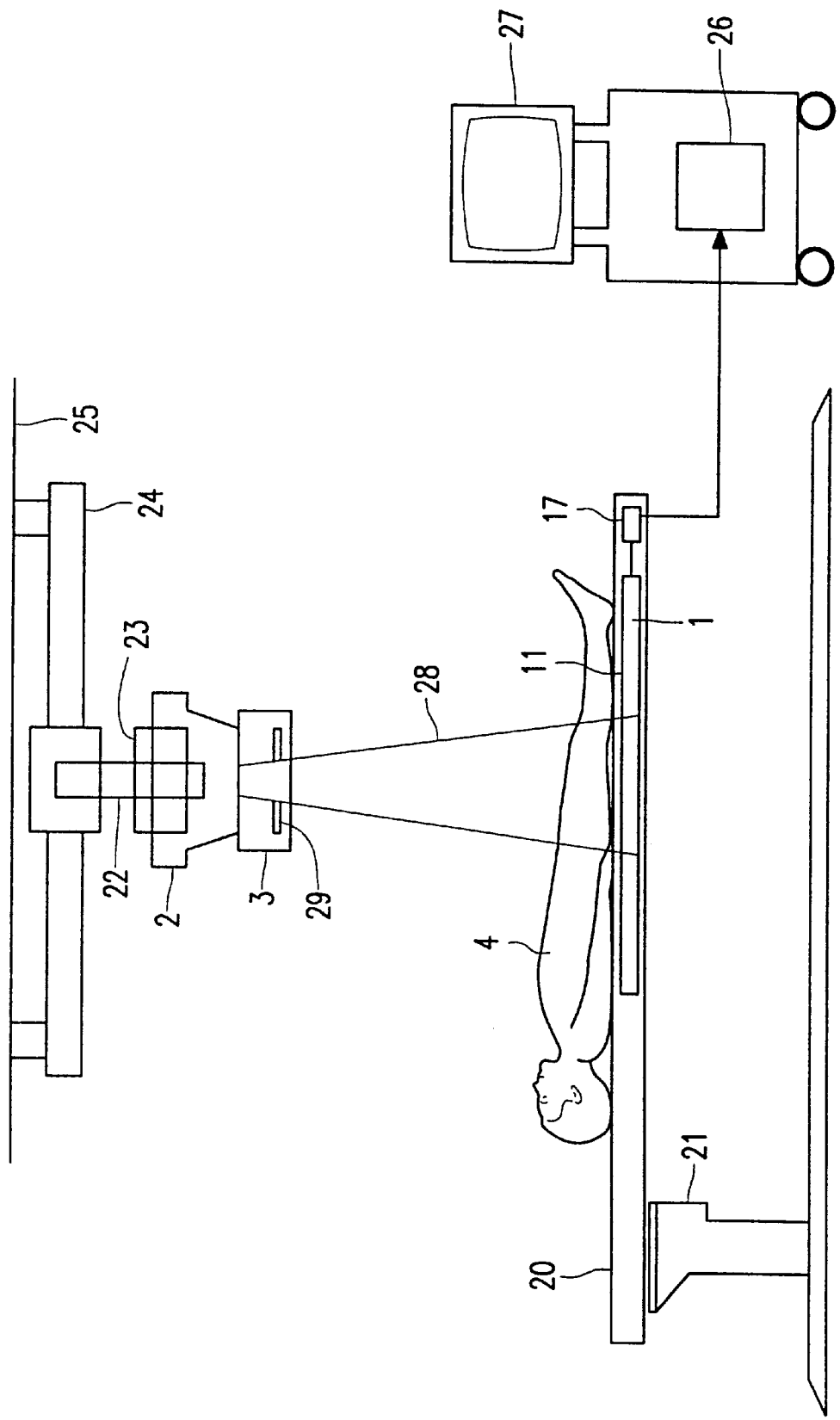
FIG. 1 is a diagrammatic side elevation of an X-ray examination apparatus in which the invention is used.

FIG. 1 shows diagrammatically an X-ray examination apparatus in which the invention is used. The X-ray examination apparatus is provided with an X-ray detector 1 which is integrated in a patient table 20. The X-ray examination apparatus also includes an X-ray source 2 which is adjustably connected to a support 22 by means of a suspension 23. The patient table 20 is mounted on a height-adjustable pillar 21. The height of the X-ray source relative to the patient 4 can be adjusted by adjustment of the position of the X-ray source 2 on the support 22 and/or of the height of the pillar 21. The suspension 23 enables displacement of the X-ray source 2 in the direction transversely to the longitudinal direction of the patient. The support 22 is suspended from rails 24 which are mounted on the ceiling 25 of the examination room in which the X-ray examination apparatus is installed. The support 22 is displaceable on the rails 24 in the longitudinal direction of the patient table.

The patient 4 is irradiated by means of an X-ray beam 28 from the X-ray source 2 in order to form an X-ray image of a part of the patient. The X-ray source 2 includes a collimator 3 with lead collimator elements 29 for spatially limiting the X-ray beam. The collimator elements 29 are displaceable transversely of the (central ray to the) X-ray beam. An X-ray image is formed on the X-ray sensitive surface 11 of the X-ray detector due to local differences in the X-ray absorption within the patient. The X-ray detector 1 is an electronic digital X-ray detector. The X-ray detector 1 converts incident X-rays into electric charges which correspond to the brightness values of the X-ray image. The X-ray detector 1 includes a read-out unit 17 which applies an image signal, for example an electronic video signal, to an image processing unit 26. The image processing unit 26 is arranged to correct he image signal at least partly for known error sources and disturbances. The processed image signal formed by the image processing unit 26 is applied to a monitor 27 in order to display the image information contained in the X-ray image.

Figure 2:
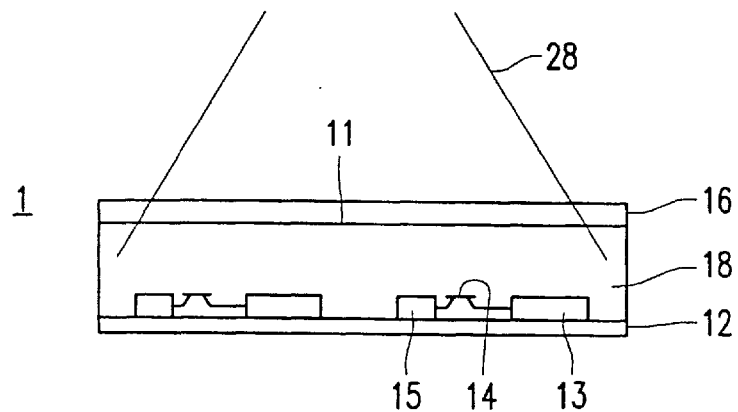
FIG. 2 is a diagrammatic representation of embodiments of an X-ray detector of an X-ray examination apparatus according to the invention.

FIG. 2 shows diagrammatically an embodiment of an X-ray detector 1, in the form of a cross-sectional view of an image sensor matrix, of an X-ray examination apparatus according to the invention. An electrode structure is provided on a glass substrate 12 by means of a thin-film technique. This structure includes collector electrodes 13 which are coupled to read-out lines 15 by way of thin-film transistors 14. The gate electrodes of the thin-film transistors are connected to addressing lines 19 which are not visible in the cross-sectional view. The present example shows only two collector electrodes, but in practice an image sensor matrix includes a large number of, for example 400 read-out lines and 400 addressing lines and 400×400 collector electrodes with thin-film transistors. The electrode structure is covered with an X-ray-sensitive layer 18 of a photoconductive material such as selenium (Se) or lead oxide (PbO). At the side of the X-ray sensitive layer which is remote from the electrode structure there is provided a common counter electrode 16. An electric voltage is applied across the X-ray sensitive layer 18 during operation. Incident X-rays generate charge carriers in the X-ray-sensitive layer, which carriers are collected in the collector electrodes and subsequently read out via the read-out lines. The X-ray-sensitive layer 18 is flat and notably has a flat surface 11 on which the X-rays are incident. Consequently, hardly any geometrical distortions occur in the X-ray image. Reading out is controlled by switching the thin-film transistors 14 by means of signals conducted by the addressing lines 19. The read-out unit 17 converts the charges read out, representing brightness values of the X-ray image, into the image signal. An image sensor matrix of this kind is known per se from European patent applications EP 0 444 720 and EP 0 440 282.

Figure 3:
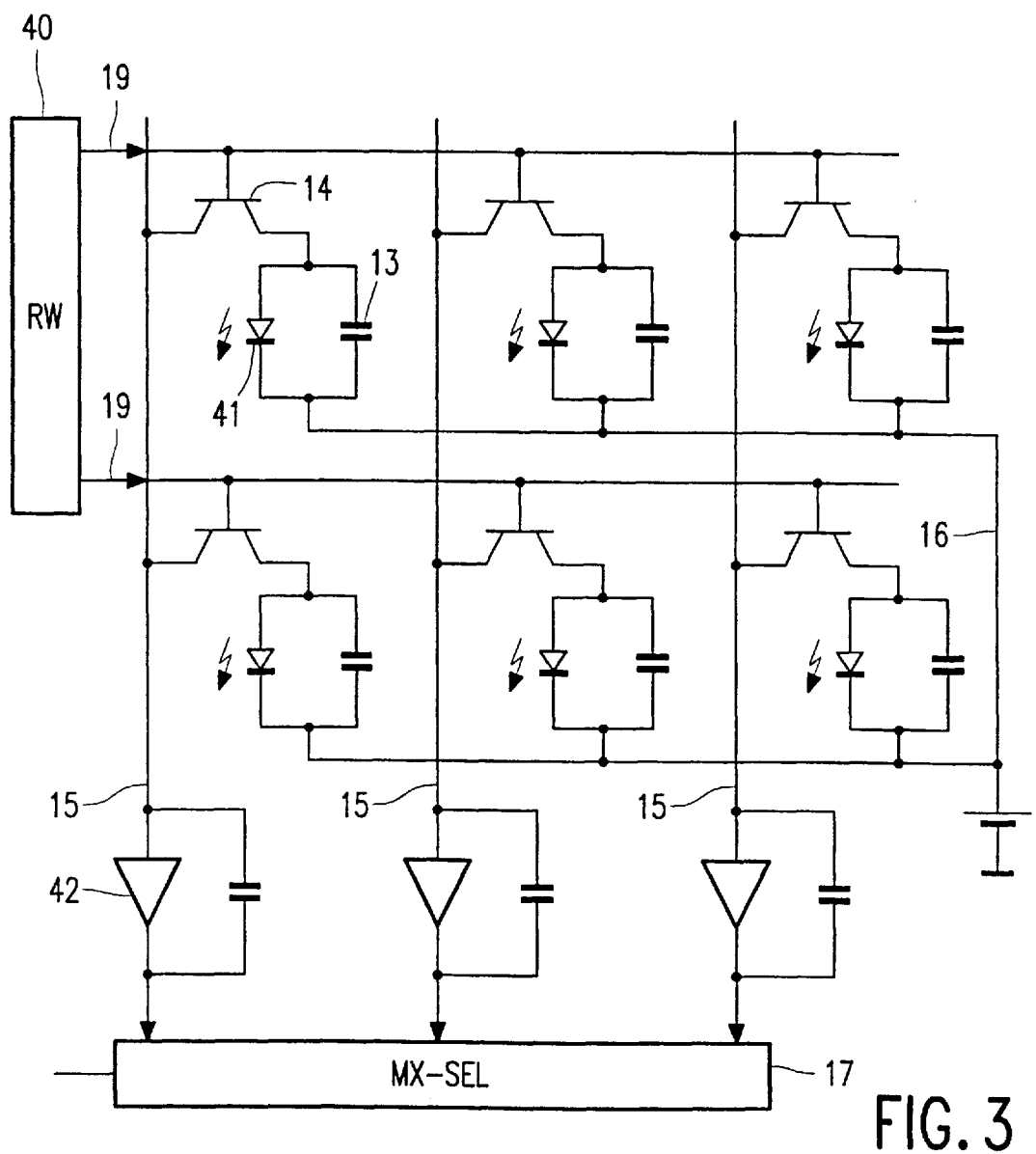
FIG. 3 is a diagrammatic representation of an electronic circuit of the X-ray detector shown in FIG. 2.

FIG. 3 shows a diagram of an electronic circuit of the X-ray detector of FIG. 2. For the sake of simplicity, the Figure shows an image sensor matrix comprising only 2×3 sensor elements. Each of the sensor elements is provided with a photodiode 41 which is connected parallel to a capacitance. In practice this capacitance is formed by the self-capacitance of the photodiode 41. The capacitances are formed each time by the relevant collector electrode 13 and the counter electrode 16. Per column the collector electrodes 13 are connected to the read-out lines 15 via the thin-film MOS transistors 14. Per row each of the thin-film transistors is connected, by way of its gate contact, to the addressing lines 19. The thin-film transistors 14 are switched per row by a row driver 40. The electric charges read from the capacitances are applied column by column to integrating read-out amplifiers 42. The integrating read-out amplifiers convert the charges of the individual columns into electric voltages which are applied to a multiplexer selector circuit 17. The multiplexer selector circuit selects parts, notably columns, of the image sensor matrix which are read out. The multiplexer selector circuit activates the integrating read-out amplifiers of the columns which are read out. The multiplexer selector circuit also acts as a read-out unit for deriving the electronic video signal, representing the X-ray image, from the electric voltages from the integrating read-out amplifiers.

Figure 4:
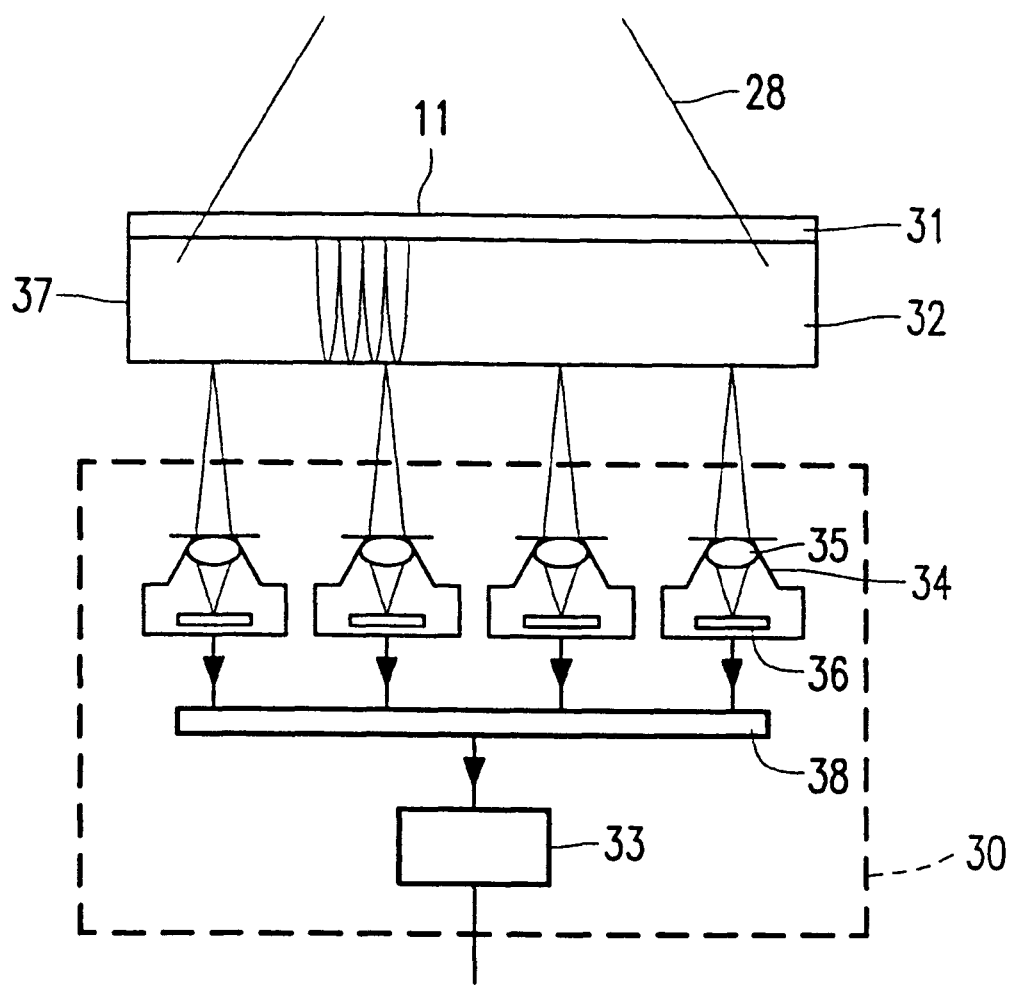
FIG. 4 is a diagrammatic representation of a further embodiment of an X-ray detector of an X-ray examination apparatus according to the invention.

FIG. 4 shows diagrammatically a further embodiment of an X-ray detector 1 of an X-ray examination apparatus according to the invention. The X-ray detector of FIG. 2 includes a conversion screen 37 which includes a scintillation layer 32 provided on a substrate 31. The substrate 31 is, for example a thin aluminum foil which suitably transmits X-rays and the scintillation layer 32 is, for example a cesium iodide layer doped with thallium or sodium (CsI:Tl, Csi:Na)). The scintillation layer converts incident X-rays into low-energetic radiation, for example red or green light. The scintillation layer has a flat surface 11 on which the X-rays 28 are incident; consequently, hardly any geometrical distortions occur in the X-ray image. The low- energetic radiation, i.e. the green or red light, emanates from the conversion screen 37 at the side of the conversion screen 37 which is remote from the X-ray source. The conversion screen 37 thus converts the X-ray image into an optical image. The scintillation layer 32 preferably contains column-shaped cesium iodide crystals which extend approximately transversely of the scintillation layer. Such crystals act as photoconductive channels which conduct the low-energetic radiation substantially perpendicularly to the scintillation layer so that the low-energetic radiation is hardly dispersed in the plane of the scintillation layer. This results in a high spatial resolution of the X-ray detector 1. The X-ray detector 1 also includes an image pick-up system 30 with a plurality of image pick-up apparatus 34 such as television cameras. Each television camera includes a camera lens 35 and an image sensor 36. Each camera lens 35 images a part of the optical image on the conversion screen 37 onto the relevant image sensor 36. Such an image sensor is, for example a charge coupled (CCD) semiconductor sensor. The individual television cameras supply sub-image signals which represent brightness values of a part of the optical image of the conversion screen. The sub-image signals are applied to a combination unit 33 via a bus 38. The combination unit derives an image signal which represents the optical image of the conversion screen from the sub-image signals. Generally speaking, the conversion screen converts the X-ray image into an optical image and the image pick-up system derives the image signal from the optical image. An X-ray detector of this kind is known per se from European patent application EP 0 583 844.

Figure 5A:
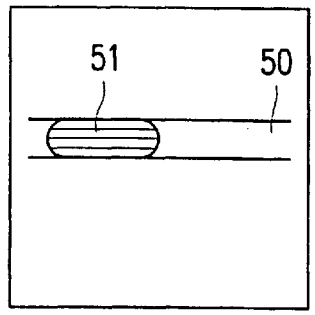
FIGS. 5a, 5b, 5c and 6a, 6b illustrate the formation of difference images from X-ray images formed by means of an X-ray examination apparatus according to the invention.
Figure 5B:
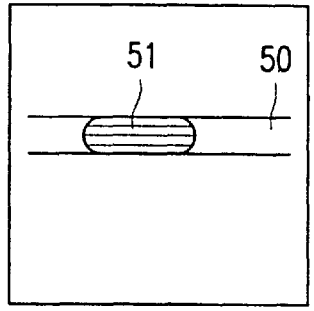
Figure 5C:
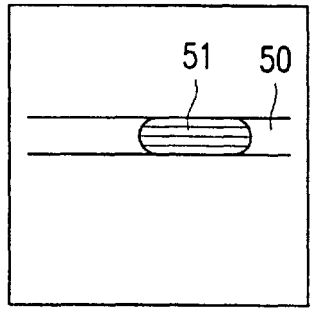
Figure 6A:
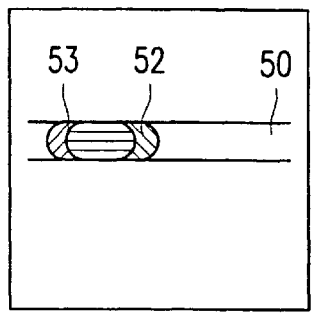
Figure 6B:
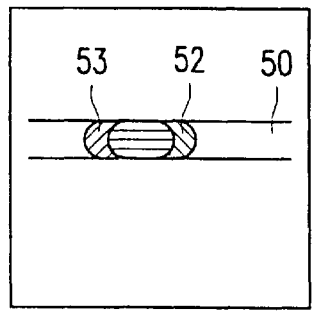
Figure 7:
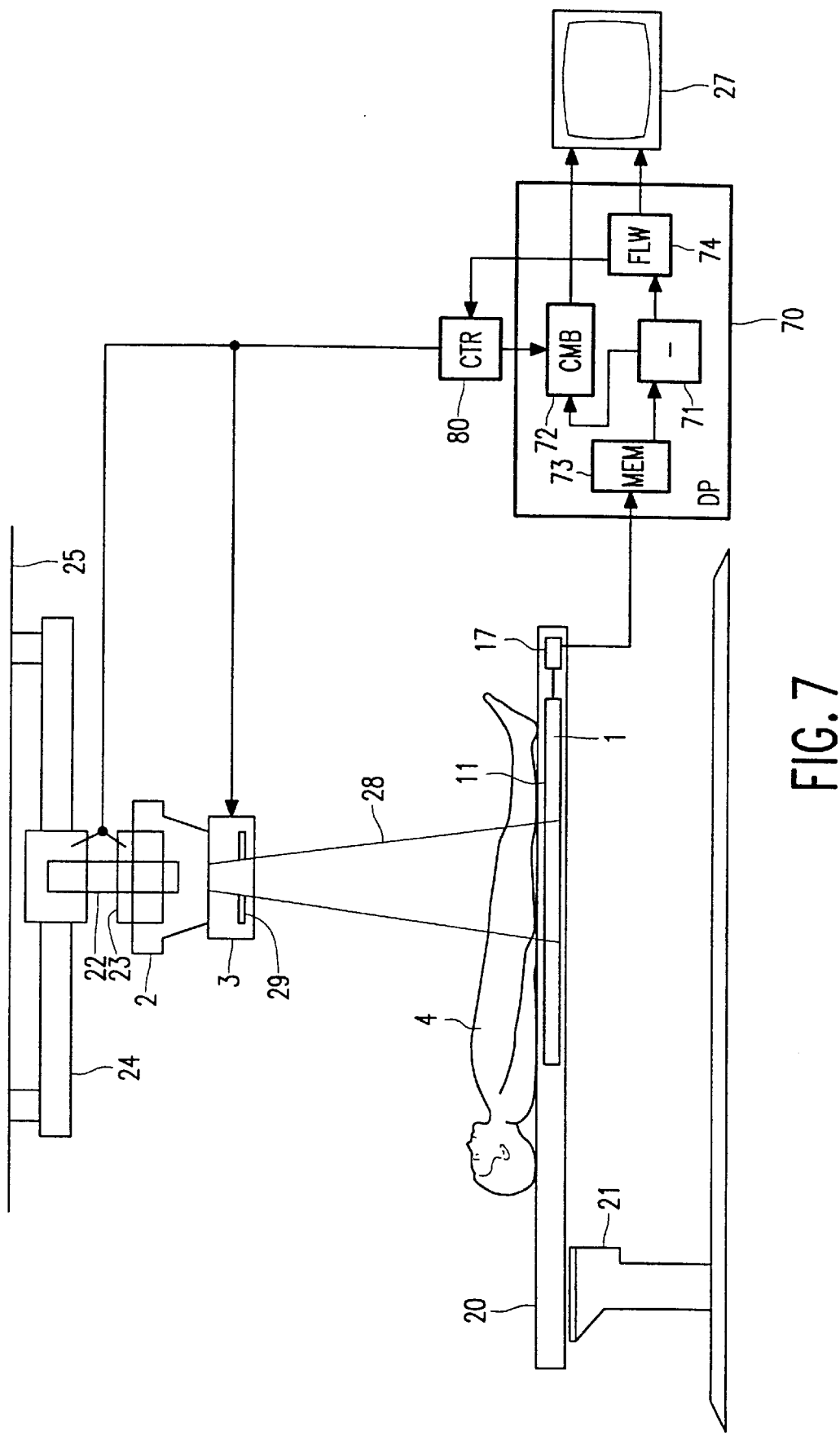
FIG. 7 is a diagrammatic side elevation of a further embodiment of an X-ray examination apparatus according to the invention.

FIGS. 5a,b,c show three successive X-ray images in which a blood vessel with locally a quantity of contrast medium is reproduced. The image shown in FIG. 5a precedes that shown in FIG. 5b which precedes that shown in FIG. 5c. As appears from the FIGS. 5a,b,c, the image of the contrast medium travels to the right in the images. FIG. 6a shows a difference image relating to the images shown in the FIGS. 5b and 5a. FIG. 6a thus contains the differences between image information in the images in the FIGS. 5b and 5a, respectively. FIG. 6a notably shows a double contrast. The double contrast includes a part 52 with brightness values which relate to a part of the image shown in FIG. 5a in which no contrast medium 51 is reproduced as yet, and a corresponding part of the image of FIG. 5b of the blood vessel 50 which has already been filled with the contrast medium. The double contrast also includes a part 53 with brightness values which relate to a part in the image in FIG. 5a which has already been passed by the contrast medium and a part in the image of the blood vessel of FIG. 5b which is still filled with the contrast medium. Similarly, FIG. 6b shows a difference image relating to the images shown in the FIGS. 5c and 5b. FIG. 6b also shows a double contrast which has been shifted in the image of the blood vessel relative to the double contrast of FIG. 6a. The displacement of the contrast medium in the blood vessel 50 can thus be accurately tracked on the basis of the shift of the double contrast 52, 53. FIG. 7 shows diagrammatically a side elevation of a further embodiment of an X-ray examination apparatus according to the invention. The image signals of the individual X-ray images picked up by means of the X-ray detector 1 are applied to a data processor 70. The data processor 70 derives the flow pattern in the blood vessels in, for example, the legs of the patient to be examined from the image signals. The image signals are temporarily stored in an image memory 73 in the data processor 70. The successive X-ray images, in which the blood vessels of the patient are reproduced, are applied to a subtraction unit 71 which derives difference image signals from the successive image signals. The difference image signals represent the difference images. Differences between the successive X-ray images are reproduced in the difference images. The individual difference images are applied to a combination unit 72. The combination unit merges the difference image signals so as to form an image signal of the assembled image which reproduces a large part of the vascular system of the patient in a single survey image. As has been explained with reference to the FIGS. 6a and 6b, the difference images contain double contrasts which represent the displacement of the contrast medium through the blood vessels. The difference image signals are applied to an arithmetic unit 74 for calculating the flow pattern in the blood vessels on the basis of the double contrast in the difference images. The arithmetic unit also calculates a graphic representation of the calculated flow pattern. The assembled image and/or the graphic representation of the flow pattern are displayed on the monitor 27. The survey image of the blood vessels, together with the flow pattern graphically represented therein, constitutes a useful technical aid for diagnosing anomalies in the blood vessels and their functioning.

The X-ray examination apparatus also includes a control unit 80 for controlling the displacement of the X-ray source and the adjustment of the collimator. The calculated flow pattern is also applied to the control unit in order to enable accurate tracking of the contrast medium in the blood vessels of the patient.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of deriving an assembled image from successive X-ray images, wherein the X-ray images are picked up by means of an X-ray detector having a predominantly flat X-ray sensitive surface such that the x-ray images are formed substantially without geometric distortions.

2. A method as claimed in claim 1 wherein the X-ray detector includes an image sensor matrix for deriving image signals from the X-ray images.

3. A method as claimed in claim 1 wherein the X-ray detector includes
   a predominantly flat conversion screen for deriving optical images from the X-ray images, and
   an image pick-up system with one or more image sensors for deriving image signals from the optical images.

4. A method as claimed in claim 1 wherein the assembled image is formed by merging image information of the successive X-ray images.

5. A method as claimed in claim 1 wherein
   the X-ray images are formed by irradiating an object to be examined by means of X-rays, after administration of a contrast medium to the object,
   difference images are derived from successive X-ray images, and
   the assembled image is derived from said difference images.

6. A method as claimed in claim 1 wherein
   three or more successive X-ray images are formed by irradiating the object to be examined
   two or more difference images are derived from the successive X-ray images,
   from time intervals between the successive X-ray images and the brightness values of the difference images a flow velocity is computed.

7. A method as claimed in claim 6 wherein the successive X-ray images are picked up at time intervals that are essentially equal.

8. A method as claimed in claim 6 wherein said time intervals between successive X-ray images are measured.

9. A method as claimed in claim 6 wherein the assembled image is formed from the difference images.

10. The method of claim 2 wherein the assembled image is formed by merging image information of the successive X-ray images.

11. The method of claim 3 wherein the assembled image is formed by merging image information of the successive X-ray images.

12. The method of claim 2 wherein
    the X-ray images are formed by irradiating an object to be examined by means of X-rays, after administration of a contrast medium to the object,
    difference images are derived from successive X-ray images, and
    the assembled image is derived from said difference images.

13. The method of claim 3 wherein
    the X-ray images are formed by irradiating an object to be examined by means of X-rays, after administration of a contrast medium to the object,
    difference images are derived from successive X-ray images, and
    the assembled image is derived from said difference images.

14. The method of claim 4 wherein
    the X-ray images are formed by irradiating an object to be examined by means of X-rays, after administration of a contrast medium to the object,
    difference images are derived from successive X-ray images, and
    the assembled image is derived from said difference images.

* * * * *